(12) United States Patent
Weinert

(10) Patent No.: US 6,740,719 B1
(45) Date of Patent: May 25, 2004

(54) PROCESS FOR REDUCING PROTEIN ALLERGENS IN LATEX PRODUCTS

(76) Inventor: George W. Weinert, 09 Cedar Point Dr., Pocasset, MA (US) 02559

( * ) Notice: Subject to any disclaimer, the term of this patent is extended or adjusted under 35 U.S.C. 154(b) by 0 days.

(21) Appl. No.: 09/646,415

(22) PCT Filed: Mar. 17, 1999

(86) PCT No.: PCT/US99/05773

§ 371 (c)(1),
(2), (4) Date: Mar. 29, 2002

(87) PCT Pub. No.: WO99/47087

PCT Pub. Date: Sep. 23, 1999

Related U.S. Application Data

(60) Provisional application No. 60/078,388, filed on Mar. 18, 1998.

(51) Int. Cl.[7] .............................. A61F 6/00; A61L 2/00; A61L 27/00; A61L 31/00; C08F 34/00
(52) U.S. Cl. ..................... 526/295; 528/934; 528/935; 2/168
(58) Field of Search ..................... 526/295; 528/934, 528/935; 2/168

(56) References Cited

U.S. PATENT DOCUMENTS

| | | |
|---|---|---|
| 1,640,363 A | 8/1927 | McGavack |
| 1,835,365 A | 12/1931 | Woodruff |
| 2,146,597 A | 2/1939 | Schwartz et al. |
| 3,417,056 A | 12/1968 | Pinazzi et al. |
| 3,650,687 A | 3/1972 | McDaniel et al. |
| 4,405,532 A | 9/1983 | Gutierrez et al. |
| 4,542,191 A | 9/1985 | Kay et al. |
| 5,321,111 A | 6/1994 | Ji |
| 5,580,942 A | 12/1996 | Cornish |
| 5,610,212 A | 3/1997 | Tanaka et al. |
| 5,620,935 A | 4/1997 | Thiele |
| 5,622,998 A | 4/1997 | Tanaka et al. |
| 5,675,026 A | 10/1997 | Thiele |
| 5,691,446 A | 11/1997 | Dove |
| 5,741,885 A | 4/1998 | Dove |
| 6,106,803 A | 8/2000 | Hasenzahl et al. |

FOREIGN PATENT DOCUMENTS

| | | |
|---|---|---|
| DE | 3021580 | 12/1981 |
| EP | 0 311 983 | 4/1989 |
| GB | 2 178 045 A | 2/1987 |

OTHER PUBLICATIONS

Dr. Donald H. Beezhold "Measurement of latex proteins by chemical and immunological methods", Guthrie Research Institute (date not indicated—appears to be Dec. 1993 based on attached "Guthrie" print out).

An Overview of the Biogel Process (1997), London International Group plc., 10 pages.

"How Gloves Are Made", Careplus—Gloves Manufacturing Process, (1998), 1 page.

George Weinert, "Latex Antigen, Glutaraldehyde, Trigger Complaints & Solutions," Advance for Medical Laboratory Professionals, Feb., 1996, pp. 10–11.

"ALERT Preventing Allergic Reactions to Natural Rubber Latex in the Workpalce," Jun. 1997, DHHS (NIOSH) Publication No. 97–135.

"Latex Labeling Required for Medical Devices," Sep. 30, 1997, FDA Talk Paper prepared by the FDA Press Office.

John W. Yunginger, M.D., et al. "Extractable latex allergens and proteins in disposable medical gloves and other rubber products," J. Allergy Clin. Immunol, vol., 93, No. 5, May, 1994, pp. 836–842.

Michael J. Brabec, Ph.D., "Aldrhydes and Acetals", Chapter 37, pp. 2628–2669 (1981).

*Primary Examiner*—Nathan M. Nutter
(74) *Attorney, Agent, or Firm*—Smith, Gambrell & Russell

(57) ABSTRACT

Described is a process for reducing the antigenicity of sap and products made from the sap of the *Hevea brasilisensis* plant and other rubber plants. The process involves contacting sap or a latex rubber product with a mono or dialdehyde, a semialdehyde or any chemical containing an aldehyde group, to cross-link antigenic proteins within the sap or the latex product. The cross-linked proteins no longer have the capability to cause an allergic reaction to persons coming into contact with the latex products made by the process of the invention. The cross-linking reaction between the proteins in the latex sap and the aldehyde can take place in the solution used to the final product, or after the final latex product has been formed, or during various intermediate steps of the processes for forming the latex products.

20 Claims, No Drawings

PROCESS FOR REDUCING PROTEIN ALLERGENS IN LATEX PRODUCTS

REFERENCE TO RELATED APPLICATION

This application claims priority on U.S. Ser. No. 60/078,388 filed on Mar. 18, 1998 which is incorporated herein in its entirety.

INDUSTRIAL APPLICABILITY

This invention relates to a process for reducing protein allergy caused by latex products, such as latex gloves and latex-containing devices used by the medical profession, which are made from the latex sap of the *Hevea brasilisensis* tree.

BACKGROUND OF THE INVENTION

It is well known that latex products, such as latex gloves, condoms, catheters and automobile tires made from the sap of the *Hevea brasilisensis* tree cause allergic reactions to some individuals who come into contact with such products. The allergic reaction is caused by the water-soluble proteins present in the sap of the tree and in the product made therewith.

In the late 1980s the United States Occupational Safety and Health Administration (OSHA) published *Bloodborne Pathogen Standards* requiring increased use of gloves to protect health care workers from exposure to the AIDS and hepatitis B viruses. Latex glove production substantially increased prior to and following the publication of such Standards. In 1991, the United States Food and Drug Administration (FDA) issued a latex alert regarding allergic reactions of patients and medical personnel who had come in contact with latex products. Among the latex products identified as potentially hazardous by the FDA were surgeon's gloves, latex exam gloves, latex condoms, barium enema retention rings and Foley catheters. The latex alert was issued after the number of annual cases regarding allergic reactions resulting from latex products increased from a few to 1,600. Of the three types of latex related diseases—dermatitis, cell mediated allergy and systemic allergy—which manifest themselves through different symptoms, cell mediated allergic response is a true allergic response, with reaction restricted to the area of contact between the glove and the skin when the glove is made from the sap of the *Hevea brasilisensis* tree. The reaction may include swelling and blistering and, after washing of the hands upon removal of the gloves, it takes from about 24 to 48 hours for the person's skin to return to normal. This allergy is caused by several water soluble proteins in latex sap.

Systemic latex allergy, the most serious of the latex-related diseases, is characterized by allergicrhinitis—asthma—and can escalate to anaphylaxis and death. This allergy is caused by several water soluble proteins in the latex sap from the *Hevea brasilisensis* tree present in products made from such sap, which proteins are dispersed in the air and are breathed in by people. Methods of measurement of airborne concentrations of latex antigen as well as latex antigen concentrations in products, such as gloves, in amount as low as 1 nanogram per cubic meter ($ng/M^3$) are known. Several healthcare institutions have decided to adopt 10 $ng/M^3$ as a ceiling concentration or standard for personal exposure.

It is known that up to 100 percent of the water soluble protein can be removed from latex of the *Hevea brasilisensis* tree by subjecting the latex to several washings with water and to centrifugation, but with each washing the latex yield decreases, thus increasing the cost of the resulting purified product. Numerous attempts have been made by others to solve the problem of allergic reactions caused to certain people when they come into contact with rubber products made from the sap of the *Hevea brasilisensis* tree due to the proteins in the sap being present in such products.

U.S. Pat. No. 5,580,942 acknowledges the severe allergic reactions in hypersensitive people caused by the proteins present in the natural rubber latex obtained from *Hevea brasilisensis* trees. The patentee has a simple solution to the problem, namely, avoiding use of the latex from the *Hevea brasilisensis* in making latex products. Instead, the patentee uses latex extracted from the *Parthenium argontatum* (guayule) plant or the *Ficus elastica* plant, which plants have a different protein profile, whereby the proteins from the sap of these plants do not cause allergic reactions in hypersensitive humans.

A review of latex measurement proteins has been published (Beezhold D. H., Measurement of latex proteins by chemical and immunological methods, Procedings of Latex Protein Allergy: The Present Position. Amsterdam, December 1993).

Proteins have been isolated from rubber particles and from the B and C serum fractions of fresh non-ammoniated latex (NAL). When analyzed by sodium dodecyl sulphate polyacrylamide gel electrophoresis (SDS-PAGE), distant protein bands are observed (Hasma, *J. Nat. Rubb. Res.*, 1992, 7(2), 102–112; Arreguin, et al., Electrophoresis, 1988, 9, 323–326; Slater, et al., *J. Allergy, Clin. Immunolo.*, 1992, 89, 673–678.). Electrophoretic profiles of NAL reveals major proteins at 46, 29 and 14 kDa, and minor bands at 90, 55, 40, 36, 24, 20 and 18 kDa. Hevein (4 kDa) and hevamine (29 kDa) are two proteins in latex sera which have been cloned and sequenced (Lee et al., *Biol Chem.*, 1991, 256, 15944–15948; Jekel et al., *Eur. J. Biochem.*, 1991, 200, 123–130). In addition, rubber particles contain the tightly bound proteins prenyltransferase (38 kDa) and rubber elongation factor (14.5 kDa) which have also been sequenced (Dennis et al., *Biol. Chem.*, 1989, 264, 18618–26; Light et al., *J. Biol. Chem.*, 1989 264, 18589–97).

Ammonification of latex alters the proteins. Storage of latex in ammonia alters the electrophoretic profiles of proteins such that SDS-PAGE profile changes from distinct bands to a smear of polypeptides with an increase in high molecular weight material (Breezhold et al., *Arch. Surg.*, 1992, 127, 1354–1357). Many, but not all, of the changes that occur are due to hydrolysis of the proteins. Since NAL serum proteins migrate primarily below 46 kDa, the appearance of high molecular weight polypeptides suggests that ammonification (and/or other compounding ingredients) induce a type of polymerization of the latex proteins that produces the larger polypeptides. This process may contribute to the allergenicity of the latex proteins. In addition, ammonification also extracts some of the rubber bound proteins (primarily rubber elongation factor) making them soluble proteins and thus potential allergens (Hasma, *J. Nat. Rubb. Res.*, 1992, 7(2), 102–112).

Much of the protein in latex is not tightly bound to the rubber, but is "water soluble" and readily leaches out of the latex. In order to measure latex proteins it is important to understand the parameters which influence extractability. It has been shown that water soluble proteins are readily extractable, however, complete extraction may take up to 18 hours or more (Dalrymple et al., *Rubb. Devel.*, 1992, 45, 51–60; Hashim, *International Rubber Technology Conference*, Kuala Lumpur, Malaysia, June 1993; Yeang et al., *International Rubber Technology Conference*, Kuala Lumpur, Malaysia, June 1993). The volume, pH, and composition of extraction buffer are also important factors.

A majority of the latex proteins have an acidic pH between 4.0 and 6.5 (Chambeyron et al., *Allergy*, 1992, 90, 230–235) that increases their solubility in basic buffers and helps explain the observation that more protein is extracted in higher pH buffers. Latex proteins are drawn to the surface of the latex during drying. The surface proteins can be collected directly from the surface by dry swabbing (Dalrymple et al., *Rubb. Devel.*, 1992, 45, 51–60). By analyzing proteins obtained from dry swabbing rubber films, a unique group of surface proteins which are nearly insoluble in water and have limited solubility in carbonate buffer was observed. These proteins migrate in SDS gels with a relative molecular mass of between 60 and 70 kDa. The proteins are remarkable in that they can be identified by their ability to non-specifically bind IgM from human serum. Furthermore, the IgM binding proteins (IgMbp) can activate the serum complement system and thereby have the potential to cause anaphylactoid reactions. Because these proteins are insoluble they are easily overlooked but must be considered as a potential source of allergens.

Attempts to identify specific allergens has resulted in a wide range of different molecular weight allergens being proposed (Chambeyron, et al., *Allergy*, 1992, 47, 92–97; Makinen-Kiljunen et al., *J. Allergy Clin. Immunol.*, 1992,90, 230–235; Jaeger et al., *Allergy Clin. Immunol.*, 1992, 89, 759–768). A recent review summarized the published data and suggested that the studies implicate two proteins of 30 kDa and 14 kDa as the common allergens (Hamann, *Amer. J. Cont. Derma.*, 1993, 4, 4–21. An abstract recently identified a 14 kDa allergen as rubber elongation factor, one of the rubber bound proteins (Czuppon et al., CHEST 104; abstract 159S, 1993).

U.S. Pat. No. 5,610,212 acknowledges that products made of natural rubber, such as rubber gloves, produce allergic reactions in some people, which reactions are attributed to the proteins present in natural rubber. The patent also discusses prior deproteinizing processes for latex which have been used to get around the problem caused by natural rubber. The patent discloses a process for markedly improving the stabilization of deproteinized natural rubber latex which has been treated with a protease and a surfactant, by addition thereto of a specific surfactant or an oligomer or polymer.

U.S. Pat. No. 5,622,998 discusses various known processes for depolymerizating natural rubber and discloses a process for forming a liquid depolymerized natural rubber which produces no immediate allergy. The patentee dissolves a deproteinized natural rubber into an organic solvent to a concentration of about 1 to 30 percent by weight and then carries out air oxidation of the resulting solution in the presence of a metallic catalyst.

BRIEF SUMMARY OF THE INVENTION

The process of the invention comprises reacting proteins in the sap of the *Hevea brasilisensis* plant and other rubber plants, which sap is used in the known processes for the manufacture of latex products, such as latex gloves or other latex-containing products, automobile tires and medical devices which are intended to come into contact with people or will be exposed to people, such as patients, doctors, nurses, laboratory technicians and others, with an aldehyde, such as a mono-aldehyde, such as formaldehyde, or a dialdehyde, such as glutaraldehyde or semialdehydes or any chemical containing an aldehyde group, to cross-link such proteins. The cross-linked proteins no longer have the capability to cause an allergic reaction to persons coming into contact with the latex products made by the process of the invention. The cross-linking reaction between the proteins in the latex sap and the aldehyde can take place in the solution used to prepare the final product, or after the final latex product has been formed, or during various intermediate steps of the known processes for forming the latex products.

DETAILED DESCRIPTION OF THE INVENTION

The invention comprises a process for significantly reducing and/or eliminating the allergy caused to certain people who come into contact with latex products made from the latex sap of the *Hevea brasilisensis* plant or any latex producing plant due to the presence of proteins from the latex sap. Processes for making such latex products are well known. Applicant has found that he can significantly decrease and/or even eliminate the presence of these proteins in the sap which causes the allergic reactions by reacting such proteins with an aldehyde, such as formaldehyde, or preferably with a dialdehyde, most preferably, glutaraldehyde. Such reaction can take place in the latex solution used in a step of the known process of making the latex product. Such aldehyde, and preferably glutaraldehyde, is added to and stirred in the latex solution in an amount sufficient to react with the proteins in the latex solution and to cross-link substantially all of the proteins into polymers. Alternatively, the reaction between the proteins in the sap of the latex and the aldehyde can take place during other steps in the known processes for making the latex products, as long as the proteins in the latex come into contact with and react with the aldehyde and are cross-linked to form a polymer. Such reaction can also take place after the latex product, such as the rubber glove, is formed. The reaction of the proteins in the latex which are on the surfaces of the latex product are reacted with the aldehyde, such as by the coating of the surface with the aldehyde, or by the immersion of the product in the aldehyde, for a period of time sufficient to completely react and cross-link the proteins with the aldehyde.

The use of an aldehyde and, particularly, glutaraldehyde, to obtain the significant reduction of protein allergies caused by latex products made from the sap of the *Hevea brasilisensis* tree is contrary to what one would be expected to use. Glutaraldehyde is one of two high-level disinfectant chemicals currently approved by the FDA for disinfecting endoscopes, bronchoscopes, cystoscopes, ultrasonic transducers and other devices not amenable to disinfection by heat, steam, radiation or other means. Glutaraldehyde presents a health hazard to persons working with it, such as red burning eyes, sore throat, nasal discharge and red itchy skin. Glutaraldehyde is also a skin sensitizer and has been known to aggravate asthma. Applicant has found that by reacting two known health hazards to humans, namely, the proteins in the latex sap of the *Hevea brasilisensis* tree and glutaraldehyde, the proteins cross-linked with the glutaraldehyde form a reaction product which eliminates the protein allergy of the latex product.

The latex with reduced allergans that is produced by the method of the invention will result in significantly increased safety for latex allergic persons who use or are exposed to the following types of latex containing products:

Emergency Equipment

Blood pressure cuffs, stethoscopes, disposable gloves, oral and nasal airways, endotracheal tubes, tourniquets, intravenous tubing, syringes and electrode pads Personal Protective Equipment Gloves, surgical masks, goggles, respirators and rubber aprons Office Supplies Rubber bands and erasers Hospital Supplies Anesthesia masks, catheters, wound drains, injection ports, rubber tops of multidose vials and dental dams Consumer Products Automobile tires, motorcycle and bicycle handgrips, carpeting, swimming goggles, racquet handles, shoe soles, expandable fabric (waistbands), dishwashing gloves, hot water bottles, condoms, diaphragms, balloons, pacifiers, and baby bottle nipples The following examples are merely illustrative of the process of the invention.

The radio-immunosorbant assay (RAST) is often used as a sensitive technique which employs radio-isotope labelled anti-IgE to measure specific IgE antibody in patient sera. The latex RAST (Pharmacia) is used to determine if specific IgE to the latex proteins is present and is semi-quantitative in determining the amount of IgE present. The assay is used primarily as a diagnostic test for latex allergy.

The RAST assay employed below is performed as a competition assay (RAST inhibition) to quantitate the amount of allergen in a latex extract. In this assay, soluble allergens in latex extracts compete for binding to latex specific IgE in pooled sera from latex allergic individuals. When soluble allergens react with the IgE, the antibody is prevented from binding to a solid phase latex allergen preparation. The amount of inhibition reflects the level of soluble allergens in the extract. The RAST inhibition assay is a very sensitive method to quantitate latex allergens.

EXAMPLES OF LATEX ALLERGAN REDUCTION BY THE PROCESS OF THE INVENTION

Example 1

1. Ammoniated latex (C.N.L from the General Latex and Chemical Corporation, Billerica, Mass.) was treated with glutaraldehyde and formaldehyde to effectively cross-link the natural rubber proteins. 20 cc of a 20% glutaraldehyde solution (Sigma Chemical, St Louis, Mo., #G6257) were added to 700 cc of latex sap. 22 cc of a 37% solution of formaldehyde (Fisher Chemical, Fair Lawn, N.J.) were added to 700 cc of latex sap. Both experiments and a control of latex sap were conducted at room temperature, which was 23 degrees centigrade (C). Ten minutes later, the formaldehyde-latex solution became gel like, indicating the cross-linking of protein had occurred. The glutaraldehyde-latex solution did not become gel-like.

2. The glutaraldehyde-latex solution was coated on a glass plate and allowed to air dry (23 degrees C for 30 minutes). A control of the untreated latex was applied to another glass plate in a similar fashion and allowed to air dry (23 degrees C for 30 minutes). The plates were incubated at 130 degrees C for 30 minutes.

3. The formed films were sent to the MAYO clinic to determine the concentration antigen by the RAST inhibition test, a test specific to measure the antigenic proteins. The control sample contained 409,140 nanograms per gram of antigenic protein, and the glutaraldehyde treated latex sample contained 42,672 nanograms per gram of antigenic protein.

4. Subsequent samples were prepared in a similar fashion described above, except the vulcanization temperature was 120 degrees centigrade. The RAST inhibition antigen testing was conducted at the IBT Reference Laboratory. The control sample contained 13.0 micrograms per gram of antigenic protein, and the glutaraldehyde treated latex sample contained 5.6 micrograms per gram of antigenic protein.

Example 2

Additional experiments were conducted using a new sample of latex and several other aldehydes.

1. Ammoniated latex (C.N.L. from the General Latex Corporation, Billerica, Mass.) was treated with formaldehyde and glutaraldehyde as confirmation of earlier experimental tests demonstrating the crosslinking of the natural rubber proteins previously discussed. In addition, samples of the latex were treated with, citronellal (Fisher Scientific, Pittsburgh, Pa., #AC405291000), butyraldehyde (Fisher Scientific, Pittsburgh, Pa., #AC220302500) and crotonaldehyde (Fisher Scientific, Pittsburgh, Pa. #AC 158220050). An aliquot of each aldehyde was added to 20 milliliters of latex dispersion. All five experiments were conducted at room temperature, which was 22 degrees centigrade (C). There was no apparent thickening in any of the five solutions.

2. Each solution was coated on a glass plate and allowed to air dry for 30 minutes at 22 degrees centigrade (C). The plates were incubated for 20 minutes at 200 degrees Fahrenheit 3. The formed films were sent to the MAYO Clinic to determine the concentration of antigen by the RAST inhibition test, a test specific to measure antigenic proteins. This control sample contained 9370 nanograms per gram of antigenic protein.

4. 400 microliters of formaldehyde were added to 20 milliliters of latex. The sample contained 2249 nanograms per gram of antigenic protein. This was a 76 percent reduction as compared to the control sample.

5. 800 microliters of glutaraldehyde were added to 20 milliliters of latex, and the sample contained 5254 nanograms per gram of antigenic protein. This was a 44 percent reduction as compared to the control sample.

6. 800 microliters of butyraldehyde were added to 20 milliliters of latex, and the sample contained 1461 nanograms per gram of antigenic protein. This was an 84 percent reduction as compared to the control sample.

7. 400 microliters of crotonaldehyde were added to 20 milliliters of latex, and the sample contained 5554 nanograms per gram of antigenic protein. This was a 41 percent reduction as compared to the control sample.

8. 200 microliters of citronellal were added to 20 milliliters of latex, and the sample contained 4515 nanograms per gram of antigenic protein. This was a 52 percent reduction as compared to the control sample.

Example 3

EXAMPLES OF LATEX ALLERGAN REDUCTION IN A TYPICAL MANUFACTURING PROCESS

A typical manufacturing sequence for a dipped product such as a glove or a condom involves sequential steps of:

1. dipping a form or mandrill into a release agent 2. air drying the release agent coated form or mandrill 3. dipping the form or mandrill into a latex solution 4. air drying the latex coated form or mandrill 5. vulcanizing the latex, and generally, 6. dipping the vulcanized product a dispersion of powder The product is then stripped from the form or mandrill and packaged. Some products, such as surgical gloves, may also be sterilized, usually by radiation.

The method of the invention can be performed at different steps of the manufacturing process. The aldehyde solution can be mixed with the latex dipping solution. Generally the aldehyde is added to the latex solution with mixing to promote uniformity. The aldehyde can also be in line blended with the latex solution to maintain a consistent depth of the dipping solution. Currently, some glove manufactures spray water on the vulcanized glove to wash away water-soluble surface protein or pass the gloves on the mandrills through a series of leaching tanks. By the method of the invention, the aldehyde can be added to the washing or leaching solutions or could be sprayed directly onto the finished product to cross-link the surface proteins.

The above examples demonstrate that substantial reductions in latex antigens can be obtained by the method of the invention.

Further variations and modifications will be apparent to those skilled in the art and are intended to be encompassed by the claims appended hereto.

I claim:

1. A process for reducing the antigenicity of proteins in latex sap comprising:

contacting a sufficient amount of an aldehyde with an antigenic latex protein to react with and cross-link the protein so as to significantly reduce the antigenicity of the protein.

2. A process for reducing the antigenicity of proteins in latex sap comprising:

forming a solution of a latex sap containing an antigenic protein, and adding a sufficient amount of an aldehyde to react with and cross-link the protein so as to significantly reduce the antigenicity of the protein.

3. A latex sap produced by the process according to claim 2.

4. The process as defined in claim 1, wherein said aldehyde is a mono-aldehyde or a dialdehyde.

5. The process as defined in claim 3, wherein said dialdehyde is glutaraldehyde.

6. The process as defined in claim 3, wherein said mono-aldehyde is formaldehyde.

7. A process for making a latex product with reduced antigenicity from latex sap containing antigenic proteins, comprising:

forming a solution of said latex sap, applying a sufficient amount of an aldehyde to a surface of the product to react with and cross-link the protein so as to significantly reduce the antigenicity of the protein, shaping said latex sap into a product, and vulcanizing said product.

8. The process as defined in claim 7, wherein said aldehyde is a mono-aldehyde or a dialdehyde.

9. The process as defined in claim 8, wherein said dialdehyde is glutaraldehyde.

10. The process as defined in claim 8 wherein said mono-aldehyde is formaldehyde.

11. A process for making a latex product with reduced antigenicity from latex sap containing antigenic proteins, comprising:

forming a solution of said latex sap, shaping said latex sap into a product, vulcanizing said product, and applying a sufficient amount of an aldehyde to a surface of the product to react with and cross-link the protein so as to significantly reduce the antigenicity of the protein.

12. The process as defined in claim 11, wherein said aldehyde is a mono-aldehyde or a dialdehyde.

13. The process as defined in claim 12, wherein said dialdehyde is glutaraldehyde.

14. The process as defined in claim 12 wherein said mono-aldehyde is formaldehyde.

15. A latex product produced by the process according to claim 7.

16. A latex product produced by the process according to claim 11.

17. In a process for making a latex product from the latex sap of the *Hevea brasilisensis* plant containing antigenic proteins which cause allergic reactions to persons coming into contact with said latex product, comprising;

forming a solution of said latex sap, shaping said latex sap into a product and vulcanizing said product, the improvement comprising the step of reacting said proteins present in said latex sap with a sufficient amount of an aldehyde to react with and cross-link said proteins, so as to significantly reduce the allergenicity of said latex product.

18. The process as defined in claim 17, wherein said aldehyde is a mono-aldehyde or a dialdehyde.

19. The process as defined in claim 18, wherein said dialdehyde is glutaraldehyde.

20. The process as defined in claim 18, wherein said mono-aldehyde is formaldehyde.

* * * * *